United States Patent
Latif

(10) Patent No.: US 11,227,387 B2
(45) Date of Patent: Jan. 18, 2022

(54) MULTI-STAGE BRAIN TUMOR IMAGE PROCESSING METHOD AND SYSTEM

(71) Applicant: Prince Mohammad Bin Fahd University, Dhahran (SA)

(72) Inventor: Ghazanfar Latif, Dhahran (SA)

(73) Assignee: Prince Mohammad Bin Fahd University, Dhahran (SA)

( * ) Notice: Subject to any disclaimer, the term of this patent is extended or adjusted under 35 U.S.C. 154(b) by 30 days.

(21) Appl. No.: 16/876,859

(22) Filed: May 18, 2020

(65) Prior Publication Data

US 2021/0358117 A1 Nov. 18, 2021

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/7275* (2013.01); *G06T 7/11* (2017.01);
(Continued)

(58) Field of Classification Search
CPC ....... G06T 7/0012; G06T 15/10; G06T 7/187; G06T 7/62; G06T 7/11;
(Continued)

(56) References Cited

U.S. PATENT DOCUMENTS

2019/0026897 A1 1/2019 Wu et al.
2020/0005461 A1* 1/2020 Yip .................. G06T 7/40
(Continued)

FOREIGN PATENT DOCUMENTS

CN 106780453 A 5/2017

OTHER PUBLICATIONS

Hossain, Tonmoy "Brain Tumor Detection Using Convolutional Neural Network" 1st International Conference on Advances in Science, Engineering and Robotics Technology. 2019 (Year: 2020).*
(Continued)

*Primary Examiner* — Emily C Terrell
*Assistant Examiner* — Molly Delaney
(74) *Attorney, Agent, or Firm* — Oblon, McClelland, Maier & Neustadt, L.L.P.

(57) ABSTRACT

Methods, systems, and computer readable media to detect and model a brain tumor in an electronic image and to predict features of the brain tumor based on the model. The method can include classifying one or more magnetic resonance imaging (MRI) images of a brain into one or more of one or more tumorous images containing an image of a tumor or one or more non-tumorous images, wherein the classification is performed using a deep learning CNN system. The method can also include segmenting a tumor region from one of the one or more tumorous images. The segmenting can include a neighboring Fuzzy C-Means (FCM) process. The method can further include classifying the segmented tumor region into one of four classes of brain tumor types. The segmented tumor region is classified as a
(Continued)

particular brain tumor type using the deep learning CNN system. The method can also include reconstructing a 3D model of the tumor region and measuring one or more of a location of the tumor, a shape of the tumor, or a volume of the tumor.

17 Claims, 5 Drawing Sheets

(51) Int. Cl.
| | |
|---|---|
| *G06T 7/62* | (2017.01) |
| *G06T 7/187* | (2017.01) |
| *G06T 15/10* | (2011.01) |
| *A61B 5/00* | (2006.01) |

(52) U.S. Cl.
CPC ............... *G06T 7/187* (2017.01); *G06T 7/62* (2017.01); *G06T 15/10* (2013.01); *G06T 2207/10088* (2013.01); *G06T 2207/20081* (2013.01); *G06T 2207/20084* (2013.01); *G06T 2207/30016* (2013.01); *G06T 2207/30096* (2013.01)

(58) Field of Classification Search
CPC . G06T 2207/30016; G06T 2207/30096; G06T 2207/20084; G06T 2207/20081; G06T 2207/10088; A61B 5/7275
See application file for complete search history.

(56) References Cited

U.S. PATENT DOCUMENTS

2020/0011950 A1    1/2020   Tiwari et al.
2020/0380688 A1*   12/2020   Abramoff ............ G06N 3/0454

OTHER PUBLICATIONS

Ozyurt, et al. ; An expert system for brain tumor detection: Fuzzy C-means with super resolution and convolutional neural network with extreme learning machine ; Medical Hypotheses 134 ; Oct. 10, 2019 ; 8 Pages.

Somasundaram, et al. ; A Hybrid Convolutional Neural Network and Deep Belief Network for Brain Tumor Detection in MR Images ; International Journal of Recent Technology and Engineering (IJRTE) ; Jul. 2019 ; 7 Pages.

Latif, et al. ; Deep CNN based MR image Denoising for tumor segmentation using watershed transform ; International Journal of Engineering & Technology 7 ; pp. 37-42 ; 6 Pages.

* cited by examiner

MULTI-STAGE BRAIN TUMOR IMAGE PROCESSING METHOD AND SYSTEM

BACKGROUND

Technical Field

The present disclosure is directed generally to computerized medical image processing methods and systems, and, more particularly, to multi-stage brain tumor image processing systems and methods of use thereof.

Description of the Related Art

Brain cancer is one of the most common causes of death and caused around 9 million deaths in 2015. The annual number of deaths attributable to brain cancer is expected to increase to an estimated 11.5 million in 2030. In order to detect brain tumors, radiologists typically analyze a large number of Magnetic Resonance Imaging (MRI) scans. Radiologists may need to recognize and/or distinguish various objects that appear similar (in terms of shape, size, or density) in the analyzed MRI scans.

Manual analysis of MRI scans by radiologists is not only time consuming but is also prone to misdiagnosis. More than one radiologist may be required to reduce chances of misdiagnosis by requiring agreement between the diagnoses of at least two radiologists. An alternative that may increase both efficiency and effectiveness of diagnosis involves use of automated computer aided diagnosis systems to process MRI scans and detect brain tumors.

The results of automated systems can be used by radiologists to cross-check a manual diagnosis.

Some implementations of the present disclosure were conceived in light of the above-mentioned problems and limitations of conventional methods and techniques for analysis of tumors based on MRI data.

SUMMARY

Some implementations include a computerized method to detect and model a brain tumor in an electronic image and to predict features of the brain tumor based on the model. The method can include classifying, using one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system. The method can also include segmenting, using the one or more processors, a tumor region from one of the one or more tumorous images, wherein the segmenting includes a neighboring Fuzzy C-Means (FCM) process. The method can further include classifying, using the one or more processors, the segmented tumor region into one of four classes of brain tumor types, wherein the segmented tumor region is classified as a particular brain tumor type using the deep learning CNN system. The method can also include reconstructing, using the one or more processors, a 3D model of the tumor region from the MRI images containing the one or more tumorous regions, and measuring, using the one or more processors, one or more of a location of the tumor, a shape of the tumor, or a volume of the tumor based on the 3D model of the tumor region. In some implementations, the measuring is based on data corresponding to one or more boundaries of the segmented tumor region.

In some implementations, the method further comprises determining the location of the brain tumor by dividing one of the one or more MRI images of the brain into one or more sections, wherein the one or more sections include at least one of a front right side, a central right side, a back right side, a central back side, a back left side, a central left side, a front left side, or a central front side. In some implementations, the method further comprises determining a volume of the brain tumor as a proportion of a volume of the brain based on a comparison of a total number of tumorous images with a total number of images.

In some implementations, the four classes include necrosis, edema, enhancing tumor, and non-enhancing tumor. In some implementations, segmenting the tumor region includes one or more of: enhancing the segmentation of the tumor region using one or more of manipulating image intensity values or using neighboring image features in conjunction with actual image features, or further enhancing the tumor region by applying a region-growing algorithm. In some implementations, applying the region-growing algorithm includes at least one of measuring a tumor size or identifying a tumor location based on data corresponding to one or more boundaries of the segmented tumor region.

Some implementations include a system to detect and model a brain tumor in an electronic image and to predict features of the brain tumor based on the model. The system can include one or more processors and a non-transitory computer readable storage having software instructions stored thereon configured to cause the one or more processors to:

classify, using the one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system;

segment, using the one or more processors, a tumor region from one of the one or more tumorous images, wherein the segmenting includes a neighboring Fuzzy C-Means (FCM) process;

classify, using the one or more processors, the segmented tumor region into one of four classes of brain tumor types, wherein the segmented tumor region is classified as a particular brain tumor type using the deep learning CNN system;

reconstruct, using the one or more processors, a 3D model of the tumor region from the MRI images containing the one or more tumorous regions; and measure, using the one or more processors, one or more of a location of the tumor, a shape of the tumor, or a volume of the tumor based on the 3D model of the tumor region.

In some implementations, the instructions are further configured to cause the one or more processors to determine one or more of a type, a volume, a shape, or a location of the brain tumor based on data corresponding to one or more boundaries of the segmented tumor region or the brain. In some implementations, the instructions are further configured to cause the one or more processors to determine the location of the brain tumor by dividing one of the one or more MRI images of the brain into one or more sections, wherein the one or more sections includes at least one of a front right side, a central right side, a back right side, a central back side, a back left side, a central left side, a front left side, or a central front side. In some implementations, the instructions are further configured to cause the one or more processors to determine a volume of the brain tumor as a proportion of a volume of the brain based on a comparison of a total number of tumorous images with a total number of images.

In some implementations, the four classes include necrosis, edema, enhancing tumor, and non-enhancing tumor. In some implementations, segmenting the tumor region includes one or more of: enhancing the segmentation of the tumor region using one or more of manipulating image intensity values or using neighboring image features in conjunction with actual image features, or further enhancing the tumor region by applying a region-growing algorithm. In some implementations, applying the region-growing algorithm includes at least one of measuring a tumor size or identifying a tumor location based on data corresponding to one or more boundaries of the segmented tumor region.

Some implementations include a non-transitory computer readable medium having instructions stored therein that, when executed by one or more processors, cause the one or more processors to perform a method to detect and model a brain tumor in an electronic image and to predict features of the brain tumor based on the model. The method can include classifying, using the one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system. The method can also include segmenting, using the one or more processors, a tumor region from one of the one or more tumorous images, wherein the segmenting includes a neighboring Fuzzy C-Means (FCM) process. The method can further include classifying, using the one or more processors, the segmented tumor region into one of four classes of brain tumor types, wherein the segmented tumor region is classified as a particular brain tumor type using the deep learning CNN system. The method can also include reconstructing, using the one or more processors, a 3D model of the tumor region from the MRI images containing the one or more tumorous regions, and measuring, using the one or more processors, one or more of a location of the tumor, a shape of the tumor, or a volume of the tumor based on the 3D model of the tumor region.

In some implementations, the method further comprises determining one or more of a type, a volume, a shape, or a location of the brain tumor based on data corresponding to one or more boundaries of the segmented tumor region or the brain. In some implementations, the method further comprises determining the location of the brain tumor by dividing one of the one or more MRI images of the brain into one or more sections, wherein the one or more sections includes at least one of a front right side, a central right side, a back right side, a central back side, a back left side, a central left side, a front left side, or a central front side. In some implementations, the method further comprises determining a volume of the brain tumor as a proportion of a volume of the brain based on a comparison of a total number of tumorous images with a total number of images.

In some implementations, the four classes include necrosis, edema, enhancing tumor, and non-enhancing tumor. In some implementations, segmenting the tumor region includes one or more of: enhancing the segmentation of the tumor region using one or more of manipulating image intensity values or using neighboring image features in conjunction with actual image features, or further enhancing the tumor region by applying a region-growing algorithm. In some implementations, applying the region-growing algorithm includes at least one of measuring a tumor size or identifying a tumor location based on data corresponding to one or more boundaries of the segmented tumor region.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in conjunction with the accompanying drawings, wherein.

DETAILED DESCRIPTION

Figure 1:
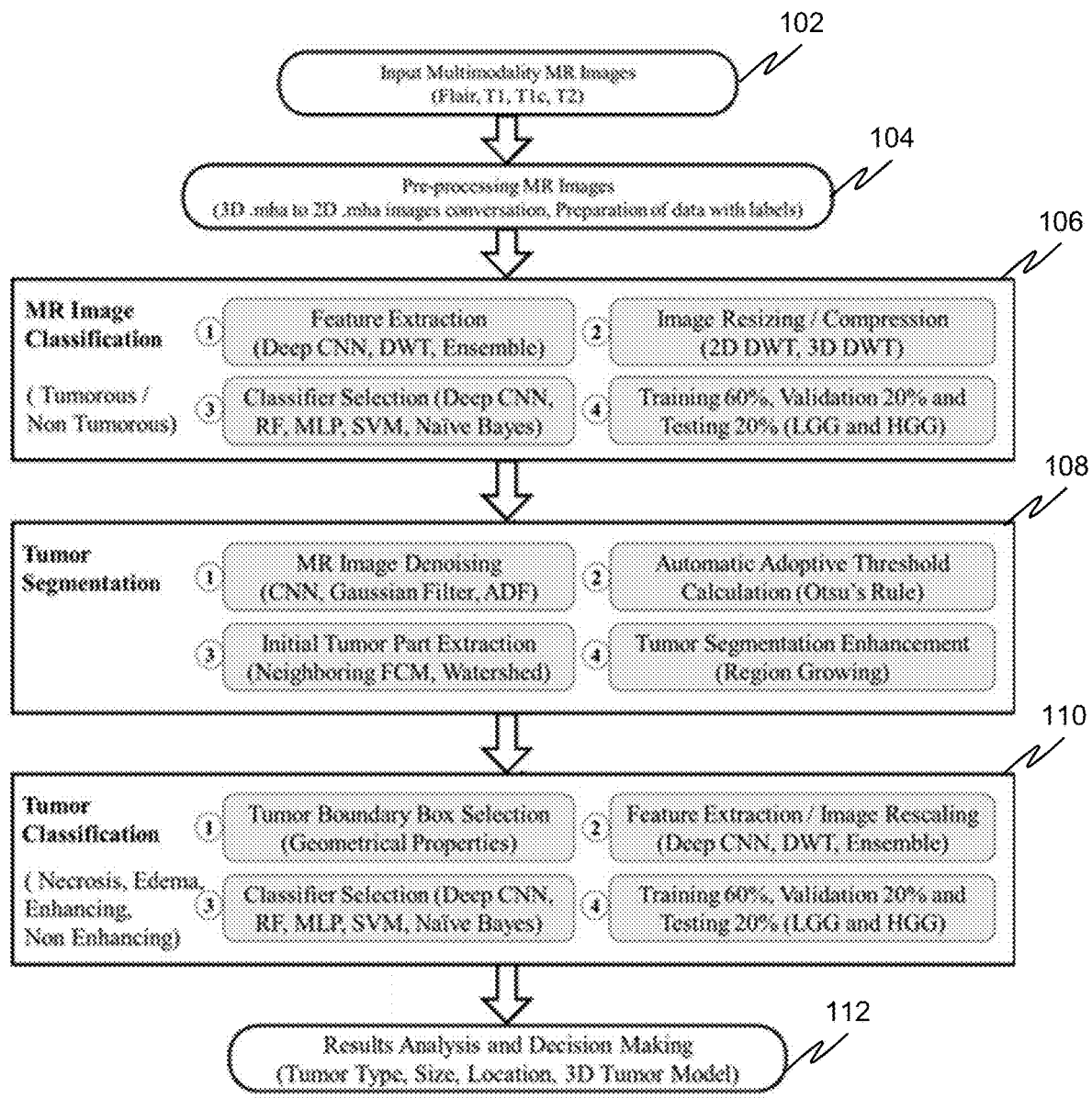
FIG. 1 shows an example workflow diagram of an exemplary multi-stage brain tumor image processing system in accordance with some implementations.

In the drawings, like reference numerals designate identical or corresponding parts throughout the several views. Further, as used herein, the words "a," "an," and the like generally carry a meaning of "one or more," unless stated otherwise. The drawings are generally drawn to scale unless specified otherwise or illustrating schematic structures or flowcharts.

In some implementations, a multi-stage image processing system detects one or more of a type, a volume, a shape, or a location of a brain tumor and generates a 3D reconstructed view and model of a brain, showing one or more detected tumors. In some implementations, the multi-stage image processing system comprises one or more of four stages. In some implementations, the first stage involves classification of magnetic resonance imaging (MRI) images into tumorous images and non-tumorous images using one or more application dependent deep learning Convolution Neural Network (CNN) architectures. To achieve accuracy, parameter manipulation is employed during classification in some implementations.

In some implementations, the second stage involves segmentation of a tumor region from one of the tumorous images using neighboring Fuzzy C-Means (FCM) based processes/techniques. In some implementations, the third stage involves parameter manipulation classification of the segmented tumor into one or more of four classes of Glioma tumors using one or more deep learning CNN architectures. In some implementations, these classes include necrosis, edema, enhancing tumors, and non-enhancing tumors. In some implementations, the fourth stage involves reconstruction of a 3D model of the tumor. In some implementations, the fourth stage involves determining one or more of a size, a location, a volume, or a type of a tumor in order to provide a model for analysis and decision making.

In some implementations, the disclosed method/system reduces the rate/chances of misdiagnosis of a tumor, and this reduction in misdiagnosis benefits the patient or customer. In some implementations, the disclosed method/system provides an option to patients to see a 3D model of the brain, including, possibly, a view of the diagnosed tumor in this 3D model. In some implementations, the disclosed method/system allows the physician/radiologist to arrive at an informed decision based on a second opinion based on this 3D model. In some implementations, the disclosed method/system provides early detection of brain tumors through automated image processing of one or more MRI images of the brain of a patient.

In some implementations, the disclosed method/system is an alternative method to manual diagnosis by radiologists and therefore provides a basis for a second opinion to the radiologists. In some implementations, the disclosed method/system reduces errors of misdiagnosis of tumors by automating the detection process and providing a validation of the radiologist's diagnosis through an automated prediction of the tumor type and tumor parameters such as a location, size, shape, or volume, etc. In some implementations, the disclosed method/system reduces the time required to process and analyze images of the brain, and more specifically, MRI scans of a brain. In some implementations, the disclosed method/system provides a detailed 3D model of the brain and/or the brain tumor region(s) to supplement the radiologist's decision making.

In some implementations, the disclosed method/system reduces healthcare costs and expenses through early detection of brain tumors, given its automated mechanism. In some implementations, the disclosed method/system can be implemented by a healthcare provider or institution, including, for example, hospitals, clinics, radiology diagnostic centers, medical education providers. In some implementations, the disclosed method/system can be used by insurance providers to approve procedures related to brain tumors and costs/expenses of such procedures. Hospitals, clinics, and radiology diagnostic centers can benefit from the disclosed method/system by using the automated images of the tumor regions to provide a computer aided second opinion to the radiologists during their analysis of brain tumor MRI scans.

FIG. 1 shows an example workflow diagram of an exemplary multi-stage brain tumor image processing system in accordance with some implementations. The workflow diagram of the disclosed method/system in accordance with some implementations is shown in FIG. 1. In some of the implementations, the disclosed method/system includes a multi-stage process comprising pre-processing, binary classification, tumor segmentation, tumor classification, and/or tumor reconstruction. In some of the implementations, the disclosed method/system receives as input one or more multimodality MRI images (e.g., fluid attenuation inversion recovery (FLAIR) MRI images) at 102.

In some implementations, at 104, the MRI images received as input are preprocessed, which can include converting 3D images to 2D images and preparation of data with labels. For example, to perform a 3D to 2D conversion, a 3D volumetric image array can be separated into 2D image slices. In some implementations, in the first stage, at 106, one or more CNN based deep learning architectures are used to classify the magnetic resonance imaging images into tumorous and non-tumorous images. In some implementations, the first stage (106) includes one or more of the following processes: 1) feature extraction including using a deep CNN, discrete wavelet transform (DWT) (see, e.g., Shensa, Mark J., *The Discrete Wavelet Transform: Wedding the A Trous and Mallat Algorithms*, IEEE Transactions On Signal Processing, Vol. 40. No. 10, October 1992, which is incorporated herein by reference), or ensemble technique, 2) image resizing and/or compression (e.g., using a 2D or 3D DWT technique) (see, Id.), 3) classifier selection (e.g., using one or more of a deep CNN, random forest (RF) (see, e.g., Donges, Niklas, A Complete Guide To The Random Forest Algorithm, https://builtin.com/data-science/random-forest-algorithm, which is incorporated herein by reference), multi-layer Perceptron (MLP) (see, e.g., Multilayer Perceptron, http://deeplearning.net/tutorial/mlp.html, which is incorporated herein by reference), support-vector machines (SVM) (see, e.g., Chang, Chih-Chung, and Lin, Chih-Jen Lin, LIBSVM: *A library for support vector machines*, ACM Transactions on Intelligent Systems and Technology, May 2011, Article No.: 27, which is incorporated herein by reference), or naïve Bayes technique (see, e.g., Zhang, Harry. "The optimality of naive Bayes." AA 1.2 (2004): 3, which is incorporated herein by reference)), and training, validation and testing (e.g., using a 60-20-20 respective distribution and high-grade glioma (HGG) and low-grade glioma (LGG) samples), which can be performed in different sequences.

In some implementations, in the second stage, at 108, the tumor area is segmented from tumorous images using one or more techniques/processes. In some implementations, a neighboring images Fuzzy C-Means (FCM) technique/process is used in conjunction with the actual image to perform the tumor segmentation. (See, e.g., M. C. J. Christ and R. M. S. Parvathi, "Fuzzy c-means algorithm for medical image segmentation," 2011 3rd International Conference on Electronics Computer Technology, Kanyakumari, 2011, pp. 33-36, which is incorporated herein by reference). In some implementations, the second stage (108) includes one or more of the following processes: image denoising (e.g., using a CNN, Gaussian filter, or anisotropic diffusion filtering (ADF), etc.), automatic adaptive threshold calculation (e.g., via Otsu's Rule, etc.), initial tumor part extraction (e.g., via neighboring fuzzy c-means (FCM) or watershed, etc.), and/or tumor segmentation enhancement (e.g., using region growing, etc.).

In some implementations, in the third stage, at 110, a multiclass tumor classification is performed to predict the tumor type. In some implementations, the third stage (110) includes one or more of the following processes: tumor boundary box selection (e.g., using geometrical properties), feature extraction and/or image rescaling (e.g., using deep CNN, DWT, or ensemble technique, etc.), classifier selection (e.g., using one or more of a deep CNN, random forest (RF), multi-layer Perceptron (MLP), support-vector machines (SVM), or naïve Bayes technique), and/or training, validation, and testing (e.g., using a 60-20-20 respective distribution and high-grade glioma (HGG) and low-grade glioma (LGG) samples). In some implementations, the classification is performed using a deep learning architecture, for example, a CNN deep learning architecture. In some implementations, the classification categorizes a brain tumor into one of four types, e.g., necrosis, edema, enhancing tumor, and non-enhancing tumor. The CNN classification process is described below in connection with FIG. 2. In some implementations, the last stage, at 112, involves results analysis and decision making. In some of the implementations, a three-dimensional (3D) reconstruction of the tumor is output at 112 along with other features such as tumor type, size, and/or location. In some implementations, at 112, boundaries of the brain and boundaries of the segmented tumors are used to measure one or more of volume or location of a tumor.

Figure 2:
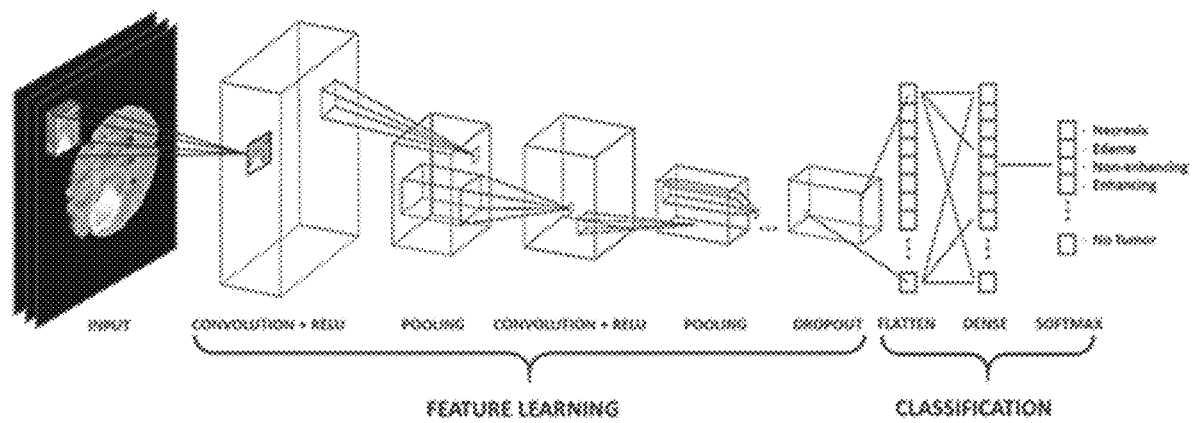
FIG. 2 is a diagram of an exemplary CNN architecture for classifying magnetic resonance imaging (MRI) images in accordance with some implementations.

FIG. 2 is a diagram of an exemplary CNN architecture for classifying MRI images in accordance with some implementations. The architecture of a CNN Model for MRI image classification in accordance with some implementations is shown in FIG. 2. In some implementations, collections of parallel feature maps are formulated using different kernels, which are then slid over an input dataset. In some implementations, these kernels are stacked together in a convolutional layer. In some of the implementations, during the creation of feature maps, a smaller dimension is used to facilitate feature sharing between the different layers. In some implementations, overlapping of kernels is avoided using zero padding of input images, which additionally facilitates management of the dimension of a convolution layer.

In some implementations, a weighted sum of an input is passed through an activation function to facilitate identification of one or more neurons that are to be rejected. In some implementations, heavier neurons are more likely to be rejected. In some implementations, different activation functions are used for different types of deep learning applications, e.g., Linear, Sigmoid, ReLU, Softmax, etc. In some implementations, after performing one or more of convolution or non-linear transformation, a pooling layer is applied to an input dataset. In some of the implementations, pooling layers down-sample data to remove noise, smoothen the data, and prevent overfitting. In some of the implementations, data points extracted from pooling layers are extended into column vectors. In some implementations, these column vectors are then used as input(s) to a classical deep neural network.

In some implementations, in the second stage, segmentation using neighboring FCM is performed. In some implementations, an advantage of segmentation using neighboring FCM over hard segmentation is that the former retains more information from the original image. In some implementations, tumor regions are extracted from tumorous images using FCM by ignoring non-tumorous images. In some implementations, to enhance segmentation, image intensity values are manipulated and neighboring image features are used along with features of the actual/target image. In some implementations, the tumor region is further enhanced by applying a region-growing algorithm. In some implementations, based on the boundaries of a segmented tumor, tumor size is measured and tumor location is identified.

In some implementations, Algorithm 1 is used to identify/detect tumor regions from a magnetic resonance imaging (MRI) image via a neighboring FCM method/technique/process.

Algorithm 1: Tumor Segmentation using Neighboring FCM Algorithm

Figure 3:
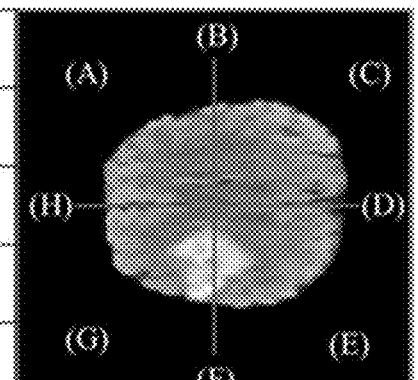
FIG. 3 shows an example distribution of a brain into 8 regions in accordance with some implementations.

Input: Z number of MRI Images of size m × n of a Patient
Output: Segmented Tumor Region TR
1.    for l = 1+2 : Z-2
2.       x = 1
3.       for j = i-2 : i+2
4.          Read image j
5.          Convert image j from uint8 to double
6.          Perform histogram equalization
7.          Set parameters for Fuzzy C-Means Clustering
8.          Apply the Standard Fuzzy C-Means Clustering Algorithm
9.          Find N Clusters by applying the Neighboring Fuzzy C-Means Algorithm
10.         Find membership function F based on Centers C of N Clusters
11.         Find threshold T[x] value based on function F and Centers C
12.         Increment x
13.       End Algorithm 1: Tumor Segmentation using Neighboring FCM Algorithm 14.         Find Threshold Ti by taking average of T[x]
15.         Compute New Clusters $C_n$ based on Ti
16.         Compute Clusters $C_n$ Perimeter $P_n$
17.         Calculate Area $A_n$ of Each Cluster in $C_n$
18.         Calculate clusters roundness $R_n = \frac{4\pi \times A_n}{P_n^2}$
19.         for k = 1 : n
20.            If $R_k$ < 0.5
21.               Discard Cluster $C_k$
22.            else
23.               $TR_i = C_k$
24.            End
25.         End
26.         Apply Region Growing Algorithm to Tumor Region $TR_i$
27.      End
28.      return TR Typically, structural parameters of brain tumors, such as the size, the shape, and the location of a brain tumor, are considered by radiologists during diagnosis. Some implementations can include a method to approximate the volume of a brain tumor and to create a 3D model of the brain tumor. The 3D model of the tumor can be reconstructed based on the tumor region segmentation of each of the 2D images processed from the 3D images. For example, once the tumor region has been detected and segmented, the 2D images with the tumor region can be reconstructed into a volumetric 3D image by placing the 2D images back into a sequence to provide a 3D image from which the tumor volume or other parameters such as location within the brain, shape, etc. can be measured or visualized. FIG. 3 shows an example distribution of a brain into 8 regions (or sections) in accordance with some implementations. The 8 regions/sections of the brain shown in FIG. 3 in accordance with some implementations include: (A) front right side, (B) central right side, (C) back right side, (D) central back side, (E) back left side, (F) central left side, (G) front left side and (H) central front side. In some implementations, the location of a brain tumor is estimated by dividing an image of the brain into the eight sections/regions mentioned above and identifying the section/region with the brain tumor based on a tumor segmentation process, e.g., step 108 of FIG. 1.

In some implementations, the coordinates of the center of a brain tumor are calculated based on the distribution shown in FIG. 3. In some implementations, the volume of a brain tumor is calculated/estimated as a proportion of the volume of the brain based on a proportion of the number of tumorous MRI images to a total number of MRI images. In some of the implementations, the volume of a brain tumor is calculated or estimated as a proportion of the volume of the brain based on a comparison of a total number of tumorous MRI images with a total number of MRI images (including both tumorous images and non-tumorous images), where the tumorous and non-tumorous images are determined based on a classification process (e.g., step 106 of FIG. 1).

Figure 4:
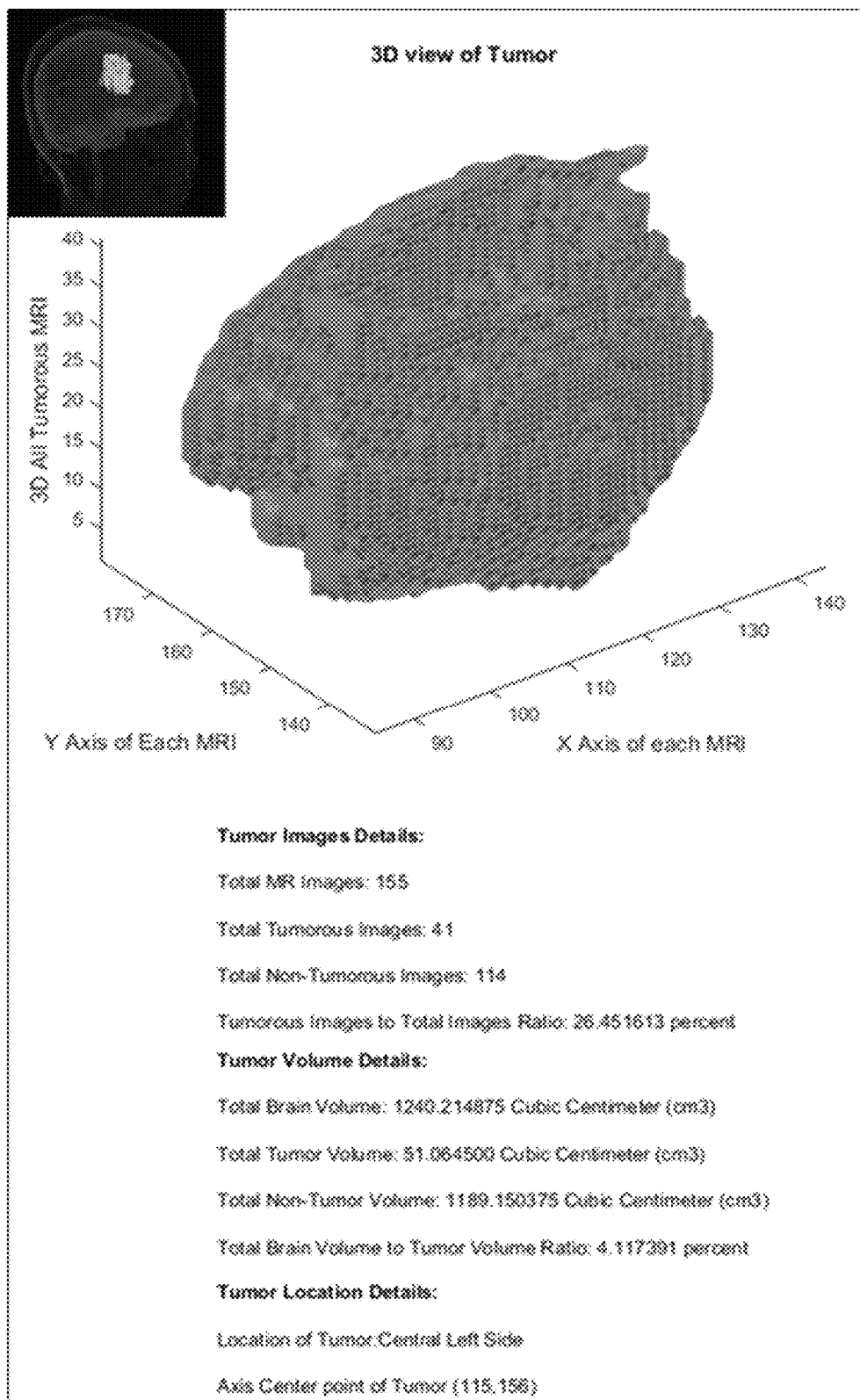
FIG. 4 is a diagram of an example 3D view of an exemplary 3D reconstruction in accordance with some implementations.

FIG. 4 is a diagram of an example 3D view of an exemplary 3D reconstruction in accordance with some implementations. FIG. 4 shows the visual results of automated brain tumor segmentation and 3D reconstruction of a brain tumor by applying FLAIR MRI images as input in accordance with some of the implementations. FLAIR (fluid-attenuated inversion recovery) is an MRI sequence used in imaging of the brain with inversion recovery set to null fluids. FLAIR can, for example, be used to suppress the cerebrospinal fluid (CSF) effects on brain images. In some implementations, the disclosed method/system estimates a volume of a brain tumor as a proportion of the volume of the brain based on a comparison of a total number of tumorous MRI images with a total number of MRI images of the brain.

A 3D model of the results of segmentation and classification in accordance with some implementations is shown in FIG. 4. In some implementations, a 3D shape of the brain tumor is approximated and visualized alongside the volume of a tumor and the volume of the brain.

Figure 5:
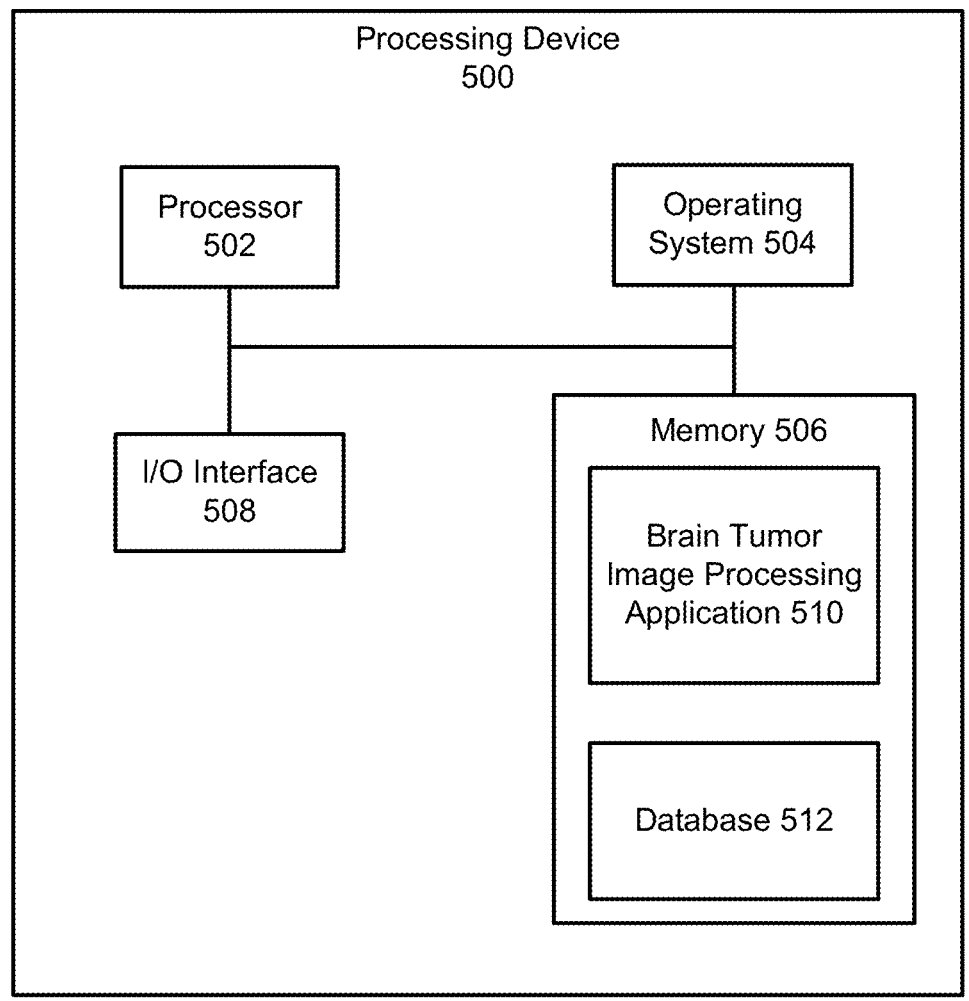
FIG. 5 is a diagram showing an example computing device configured to process brain tumor images in accordance with some implementations.

FIG. 5 is a block diagram of an example processing device 500 which may be used to implement one or more features described herein. In one example, device 500 may be used to implement a computer device or system to process the images of brain tumors as described herein and perform the appropriate method implementations described herein. Device 500 can be any suitable computer system, server, or other electronic or hardware device. For example, the device 500 can be a mainframe computer, desktop computer, workstation, portable computer, or electronic device (portable device, mobile device, cell phone, smart phone, tablet computer, television, TV set top box, personal digital assistant (PDA), media player, game device, wearable device, etc.). In some implementations, device 500 includes a processor 502, an operating system 504, a memory 506, and input/output (I/O) interface 508.

Processor 502 can be one or more processors and/or processing circuits to execute program code and control basic operations of the device 500. A "processor" includes any suitable hardware and/or software system, mechanism or component that processes data, signals or other information. A processor may include a system with a general-purpose central processing unit (CPU), multiple processing units, dedicated circuitry for achieving functionality, or other systems. Processing need not be limited to a particular geographic location or have temporal limitations. For example, a processor may perform its functions in "real-time," "offline," in a "batch mode," etc. Portions of processing may be performed at different times and at different locations by different (or the same) processing systems. A computer may be any processor in communication with a memory.

Memory 506 is typically provided in device 500 for access by the processor 502, and may be any suitable processor-readable storage medium, e.g., random access memory (RAM), read-only memory (ROM), Electrical Erasable Read-only Memory (EEPROM), Flash memory, etc., suitable for storing instructions for execution by the processor, and located separate from processor 502 and/or integrated therewith. Memory 506 can store software operated on device 500 by processor 502 and can include an operating system 504, one or more applications 510, and a database 512. In some implementations, applications 510 can include instructions that enable processor 502 to perform the functions described herein (e.g., in FIG. 1 and FIG. 4).

For example, application 510 can include methods/processes/techniques to process brain tumor images as described herein. Any of the software in memory 504 can alternatively be stored on any other suitable storage location or computer-readable medium. In addition, memory 504 (and/or other connected storage device(s)) can store machine learning model (e.g., CNN) information and/or other instructions and data used in the features described herein. Memory 504 and any other type of storage (magnetic disk, optical disk, magnetic tape, or other tangible media) can be considered "storage" or "storage devices."

I/O interface 508 can provide functions to enable interfacing of the processing device 500 with other systems and devices. For example, network communication devices, storage devices (e.g., memory and/or database), and input/output devices can communicate via interface 508. In some implementations, the I/O interface 508 can connect to interface devices, including input devices (keyboard, pointing device, touchscreen, microphone, camera, scanner, etc.) and/or output devices (display device, speaker devices, printer, motor, etc.).

For ease of illustration, FIG. 5 shows one block for each of processor 502, memory 506, I/O interface 508, and software block 510. These blocks may represent one or more processors or processing circuitries, operating systems, memories, I/O interfaces, applications, and/or software modules. In other implementations, device 500 may not have all of the components shown and/or may have other elements, including other types of elements instead of, or in addition to, those shown herein.

In general, a computer that performs the processes described herein can include one or more processors and a memory (e.g., a non-transitory computer readable medium). The process data and instructions may be stored in the memory. These processes and instructions may also be stored on a storage medium such as a hard drive (HDD) or a portable storage medium or may be stored remotely. Note that each of the functions of the described embodiments may be implemented by one or more processors or processing circuits. A processing circuit can include a programmed processor, as a processor includes circuitry. A processing circuit/circuitry may also include devices such as an application specific integrated circuit (ASIC) and conventional circuit components arranged to perform the recited functions. The processing circuitry can be referred to interchangeably as circuitry throughout the disclosure. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk, or any other information processing device.

The processor may contain one or more processors and may even be implemented using one or more heterogeneous processor systems. According to certain implementations, the instruction set architecture of the processor can use a reduced instruction set architecture, a complex instruction set architecture, a vector processor architecture, a very large instruction word architecture. Furthermore, the processor can be based on the Von Neumann model or the Harvard model. The processor can be a digital signal processor, an FPGA, an ASIC, a PLA, a PLD, or a CPLD. Further, the processor can be an x86 processor by Intel or by AMD, an ARM processor, a Power architecture processor by, e.g., IBM, a SPARC architecture processor by Sun Microsystems or by Oracle, or other known CPU architecture.

The functions and features described herein may also be executed by various distributed components of a system. For example, one or more processors may execute the functions, wherein the processors are distributed across multiple components communicating in a network. The distributed components may include one or more client and server machines, which may share processing in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes, and algorithms described herein may be performed in hardware or software executed by hardware, including computer processors and/or programmable circuits configured to execute program code and/or computer instructions to execute the functions, processes, and algorithms described herein. Additionally, an implementation may be performed on modules or hardware not identical to those described. Accordingly, other implementations are within the scope that may be claimed.

The invention claimed is:

1. A computerized method to detect and model a brain tumor in an electronic image and to predict features of the brain tumor based on the model, the method comprising:
    classifying, using one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system;
    segmenting, using the one or more processors, a tumor region from one of the one or more tumorous images, wherein the segmenting includes a neighboring Fuzzy C-Means (FCM) process;
    classifying, using the one or more processors, the segmented tumor region into one of four classes of brain tumor types selected from the group consisting of necrosis, edema, enhancing tumor, and non-enhancing tumor, wherein the segmented tumor region is classified as a particular brain tumor type using the deep learning CNN system;
    reconstructing, using the one or more processors, a 3D model of the tumor region from the MRI images containing the one or more tumorous regions; and
    measuring, using the one or more processors, one or more of a location of the tumor, a shape of the tumor, or a volume of the tumor based on the 3D model of the tumor region.

2. The method of claim 1, wherein segmenting the tumor region includes one or more of: enhancing the segmentation of the tumor region using one or more of manipulating image intensity values or using neighboring image features in conjunction with actual image features, or further enhancing the tumor region by applying a region-growing algorithm.

3. The method of claim 2, wherein applying the region-growing algorithm includes at least one of measuring a tumor size or identifying a tumor location based on data corresponding to one or more boundaries of the segmented tumor region.

4. The method of claim 1, wherein the measuring is based on one or more boundaries of the segmented tumor region or one or more image features of the brain.

5. The method of claim 4, further comprising:
    determining the location of the brain tumor by dividing one of the one or more MRI images of the brain into one or more sections, wherein the one or more sections includes at least one of a front right side, a central right side, a back right side, a central back side, a back left side, a central left side, a front left side, or a central front side.

6. The method of claim 1, wherein the measuring includes determining a volume of the brain tumor as a proportion of a volume of the brain based on a comparison of a total number of tumorous images with a total number of images.

7. A system to detect and model a brain tumor in an electronic image and to predict features of the brain tumor based on the model, the system comprising:
    one or more processors and a non-transitory computer readable storage having software instructions stored thereon configured to cause the one or more processors to:
    classify, using the one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system;
    segment, using the one or more processors, a tumor region from one of the one or more tumorous images, wherein the segmenting includes a neighboring Fuzzy C-Means (FCM) process and one or more of: enhancing the segmentation of the tumor region using one or more of manipulating image intensity values or using neighboring image features in conjunction with actual image features, or further enhancing the tumor region by applying a region-growing algorithm;
    classify, using the one or more processors, the segmented tumor region into one of four classes of brain tumor types, wherein the segmented tumor region is classified as a particular brain tumor type using the deep learning CNN system;
    reconstruct, using the one or more processors, a 3D model of the tumor region from the MRI images containing the one or more tumorous regions; and
    measure, using the one or more processors, one or more of a location of the tumor, a shape of the tumor, or a volume of the tumor based on the 3D model of the tumor region.

8. The system of claim 7, wherein the four classes include necrosis, edema, enhancing tumor, and non-enhancing tumor.

9. The system of claim 7, wherein applying the region-growing algorithm includes at least one of measuring a tumor size or identifying a tumor location based on data corresponding to one or more boundaries of the segmented tumor region.

10. The system of claim 7, wherein the instructions are further configured to cause the one or more processors to:
    determine one or more of a type, a volume, a shape, or a location of the brain tumor based on data corresponding to one or more boundaries of the segmented tumor region or the brain.

11. The system of claim 10, wherein the instructions are further configured to cause the one or more processors to:
    determine the location of the brain tumor by dividing one of the one or more MRI images of the brain into one or more sections, wherein the one or more sections includes at least one of a front right side, a central right side, a back right side, a central back side, a back left side, a central left side, a front left side, or a central front side.

12. The system of claim 7, wherein the instructions are further configured to cause the one or more processors to:
    determining a volume of the brain tumor as a proportion of a volume of the brain based on a comparison of a total number of tumorous images with a total number of images.

13. A non-transitory computer readable medium having instructions stored therein that, when executed by one or more processors, cause the one or more processors to perform a method to detect and model a brain tumor in an electronic image and to predict features of the brain tumor based on the model, the method comprising:
    classifying, using the one or more processors, one or more magnetic resonance imaging (MRI) images of a brain into one or more of one or more tumorous images containing an image of a tumor or one or more non-tumorous images, wherein the classification is performed using a deep learning Convolution Neural Network (CNN) system;
    segmenting, using the one or more processors, a tumor region from one of the one or more tumorous images, wherein the segmenting includes a neighboring Fuzzy C-Means (FCM) process;
    classifying, using the one or more processors, the segmented tumor region into one of four classes of brain tumor types selected from the group consisting of necrosis, edema, enhancing tumor, and non-enhancing tumor, wherein the segmented tumor region is classified as a particular brain tumor type using the deep learning CNN system;
    reconstructing, using the one or more processors, a 3D model of the tumor region from the MRI images containing the one or more tumorous regions; and
    measuring, using the one or more processors, one or more of a location of the tumor, a shape of the tumor, or a volume of the tumor based on the 3D model of the tumor region.

14. The non-transitory computer readable medium of claim 13, wherein segmenting the tumor region includes one or more of: enhancing the segmentation of the tumor region using one or more of manipulating image intensity values or using neighboring image features in conjunction with actual image features, or further enhancing the tumor region by applying a region-growing algorithm.

15. The non-transitory computer readable medium of claim 14, wherein applying the region-growing algorithm includes at least one of measuring a tumor size or identifying a tumor location based on data corresponding to one or more boundaries of the segmented tumor region.

16. The non-transitory computer readable medium of claim 13, further comprising:
    determining one or more of a type, a volume, a shape, or a location of the brain tumor based on data corresponding to one or more boundaries of the segmented tumor region or the brain.

17. The non-transitory computer readable medium of claim 16, further comprising:
    determining the location of the brain tumor by dividing one of the one or more MRI images of the brain into one or more sections, wherein the one or more sections includes at least one of a front right side, a central right side, a back right side, a central back side, a back left side, a central left side, a front left side, or a central front side.

* * * * *